United States Patent
Tobey et al.

(10) Patent No.: US 9,926,196 B2
(45) Date of Patent: Mar. 27, 2018

(54) PROCESSES FOR THE CONVERSION OF BIOMASS TO OXYGENATED ORGANIC COMPOUND, APPARATUS THEREFOR AND COMPOSITIONS PRODUCED THEREBY

(71) Applicants: Richard E. Tobey, St. Charles, IL (US); Jianxin Du, Naperville, IL (US); Ralph Corley, Pensacola Beach, FL (US)

(72) Inventors: Richard E. Tobey, St. Charles, IL (US); Jianxin Du, Naperville, IL (US); Ralph Corley, Pensacola Beach, FL (US)

(73) Assignee: Synata Bio Inc., Warrenville, IL (US)

( * ) Notice: Subject to any disclaimer, the term of this patent is extended or adjusted under 35 U.S.C. 154(b) by 260 days.

(21) Appl. No.: 14/512,082

(22) Filed: Oct. 10, 2014

(65) Prior Publication Data
US 2015/0028260 A1    Jan. 29, 2015

Related U.S. Application Data

(62) Division of application No. 13/304,902, filed on Nov. 28, 2011, now Pat. No. 8,895,274.

(51) Int. Cl.
*C01B 3/02* (2006.01)
*C01B 3/36* (2006.01)
(Continued)

(52) U.S. Cl.
CPC .............. *C01B 3/02* (2013.01); *C01B 3/36* (2013.01); *C12M 21/12* (2013.01); *C12M 45/06* (2013.01); *C12P 7/065* (2013.01); *C12P 7/08* (2013.01); *C12P 7/16* (2013.01); *C12P 7/52* (2013.01); *C12P 7/54* (2013.01); *B01D 2257/408* (2013.01); *C01B 2203/0255* (2013.01); *C01B 2203/043* (2013.01); *C01B 2203/048* (2013.01); *C01B 2203/0415* (2013.01); *C01B 2203/0475* (2013.01); *C01B 2203/0485* (2013.01); *C01B 2203/0495* (2013.01); *C01B 2203/0877* (2013.01); *C01B 2203/0894* (2013.01); *C01B 2203/141* (2013.01); *C01B 2203/142* (2013.01);
(Continued)

(58) Field of Classification Search
None
See application file for complete search history.

(56) References Cited

U.S. PATENT DOCUMENTS

| 4,189,307 A * | 2/1980 | Marion ..................... C01B 3/52 252/373 |
| 9,783,417 B2 * | 10/2017 | Chandran ................. C01B 3/52 |
| 2014/0252276 A1 * | 9/2014 | Chandran ................. C01B 3/52 252/373 |

\* cited by examiner

*Primary Examiner* — Wayne Langel
(74) *Attorney, Agent, or Firm* — Cardinal Law Group (57) ABSTRACT

Processes are disclosed for the conversion of biomass to oxygenated organic compound using a simplified syngas cleanup operation that is cost effective and protects the fermentation operation. The processes of this invention treat the crude syngas from the gasifier by non-catalytic partial oxidation. The partial oxidation reduces the hydrocarbon content of the syngas such as methane, ethylene and acetylene to provide advantageous gas feeds for anaerobic fermentations to produce oxygenated organic compounds such as ethanol, propanol and butanol. Additionally, the partial oxidation facilitates any additional cleanup of the syngas as may be required for the anaerobic fermentation. Producer gases and partial oxidation processes are also disclosed.

19 Claims, 1 Drawing Sheet

(51) Int. Cl.
*C12M 1/00* (2006.01)
*C12P 7/06* (2006.01)
*C12P 7/08* (2006.01)
*C12P 7/16* (2006.01)
*C12P 7/52* (2006.01)
*C12P 7/54* (2006.01)

(52) U.S. Cl.
CPC .. *C01B 2203/146* (2013.01); *C01B 2203/169* (2013.01); *C01B 2203/1671* (2013.01); *C01B 2203/1676* (2013.01); *Y02E 50/10* (2013.01); *Y02E 50/16* (2013.01); *Y02E 50/17* (2013.01)

PROCESSES FOR THE CONVERSION OF BIOMASS TO OXYGENATED ORGANIC COMPOUND, APPARATUS THEREFOR AND COMPOSITIONS PRODUCED THEREBY

CROSS REFERENCE TO RELATED APPLICATION

This application is a divisional application that claims priority from application U.S. Ser. No. 13/304,902, filed on Nov. 28, 2011, that has received a Notice of Allowance dated Aug. 6, 2014, and which is incorporated herein by reference in its entirety.

FIELD OF THE INVENTION

This invention pertains to processes and apparatus for converting biomass to oxygenated organic compound in a commercially attractive manner and to producer gas compositions.

BACKGROUND

Numerous proposals exist for the gasification of biomass to produce gases containing carbon monoxide, hydrogen and carbon dioxide. For purposes herein, the gases from gasification operations are referred to as synthesis gas (syngas). Anaerobic fermentations of carbon monoxide and hydrogen and carbon dioxide have also been proposed and involve the contact of the substrate gas in a liquid, aqueous menstruum with microorganisms capable of generating oxygenated organic compounds such as ethanol, acetic acid, propanol and n-butanol. The production of these oxygenated organic compounds requires significant amounts of hydrogen and carbon monoxide. For instance, the theoretical equations for the conversion of carbon monoxide and hydrogen to ethanol are:

$$6CO+3H_2O \rightarrow C_2H_5OH+4CO_2$$

$$6H_2+2CO_2 \rightarrow C_2H_5OH+3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

The microorganisms for the anaerobic fermentation of syngas can be adversely affected by components contained in syngas. See, for instance, Xu, et al., *The Effects of Syngas Impurities on Syngas Fermentation to Liquid Fuels*, Biomass and Bioenergy, 35 (2011), 2690-2696; United States Published Patent Application No. 20110097701; Abubackar, et al., *Biological Conversion of Carbon Monoxide: Rich Syngas or Waste Gases to Bioethanol*, Biofuels, Bioproducts & Biorefining, 5, (2011), 93-114; and Munasinghe, et al., *Biomass-derived Syngas Fermentation into Biofuels: Opportunities and Challenges*, Bioresource Technology, 101, (2011), 5013-5022.

Numerous processes have been suggested for the cleanup of syngas for anaerobic fermentation. Often, the processes involve multiple operations to remove different adverse components from the syngas. Xu, et al., state at page 2692:

"Syngas impurities may or may not need to be removed depending upon the effect of the impurity on the biological process and the environment. Selection of commercial technologies suitable for syngas cleanup is mainly based on affordability and the ability to meet end user specifications . . . . Currently, tar cracking methods (including cracking within the gasifier) can effectively convert the heavy and light hydrocarbons to negligible levels. Water quench scrubbers can be employed for removal of ammonia and trace impurities. Accordingly, amine treatment can be utilized for sulfur and $CO_2$ treatment after cooling down the syngas. Zinc oxide beds can also be added for additional sulfur removal down to low levels meeting the requirement for fuel synthesis . . . . For fermentation processes using $CO_2$ as one of the substrates, a different sulfur treatment method should be considered. Alternatively, $H_2S$ can be removed from the gasification processes by using regenerable mixed oxide sorbents such as Zinc titanates . . . ."

"Hot catalytic gas conditioning downstream of the gasifier demonstrates more advantages than physical strategies (scrubber+filter). Catalytic strategies provide the possibility to transform the impurities (especially tars and ammonia) into useful gas compounds. By adding cobalt and nickel promoters to Zn—Ti sorbents, both $NH_3$ decomposition and $H_2S$ adsorption will occur simultaneously. Most literature has centered on converting tars into useful gases on basic (calcined dolomites) and alumina-supported nickel catalysts at temperatures between 973 and 1173 K. The coupling of a guard bed made from calcined dolomite with a nickel catalytic unit can effectively reduce tar levels to a few ppms . . . ."

Syngas is typically more expensive than equivalent heat content amounts of fossil fuels. Hence, a desire exists to use syngas efficiently both in the fermentation operation to make higher value products and in conserving the syngas values in any cleanup operation. The financial viability of any conversion process, especially to commodity chemicals such as ethanol and acetic acid, will be dependent upon capital costs as well as the efficiency of conversion of the carbon monoxide and hydrogen to the sought products and the energy costs to effect the conversion.

The cleanup of syngas from biomass is further complicated since biomass is subject to variabilities that can affect gasifier performance and syngas composition. Moreover, a gasifier may from time to time change types of biomass being gasified which may also result in changes in gasifier performance and syngas composition. Thus variabilities in concentrations of components adverse to the fermentation operation, such as hydrogen cyanide, nitric oxide, acetylene and ethylene, occur. Consequently, any cleanup operation would need to have sufficient capacity to handle peak amounts of impurities. Also, the cleanup operation would have to have sufficient turndown capabilities as may be required for cleaner syngas from the gasifier and for startup and non-steady-state operations.

For a biomass to oxygenated organic compound fermentation process to be commercially viable, capital and operating costs must be sufficiently low that it is at least competitive with alternative biomass to oxygenated organic compound processes. For instance, ethanol is currently commercially produced from corn and cane sugar in facilities having name plate capacities of over 100 million gallons per year at sufficiently low costs to be competitive with fossil fuels. Biomass to oxygenated organic compound fermentation processes face even greater challenges due to the multiple major operations required to convert the biomass to syngas, cleanup the syngas sufficiently to be used in an anaerobic fermentation, effect the anaerobic fermentation and then recover a merchantable product.

United States Published Patent Application No. 20100237290 discloses a method for producing a purified syngas from the severe pyrolysis of biomass comprising removing dust and sulfur compounds from the pyrolysis gas, then subjecting the pyrolysis gas to partial oxidation at pressures suitable for conducting a Fischer-Tropsch synthesis and rapidly cooling the gas to a temperature of between 300° C. and 500° C. The patent applicants state that their purified synthesis gas can be used as a feedstock of a Fischer-Tropsch synthesis unit for making liquid fuels and for the synthesis of ammonia, alcohols or dimethyl ether. The patent applicants do not disclose or suggest the use of their purified syngas for anaerobic fermentation nor do they provide any indication of the content in the purified syngas of components that can adversely affect fermentation. Indeed, such components such as benzene and higher aromatics, ethylene and other alkenes, and acetylene and other alkylenes would be desirable in a feedstream to a Fischer-Tropsch synthesis unit.

Processes are sought to convert biomass to oxygenated organic compound at low capital and operating cost but yet provide sufficient robustness that variations in biomass feedstock and gasifier performance can occur without adversely affecting syngas fermentation. Accordingly, the processes need to be characterized by cost-effective syngas cleanup with minimal loss of carbon monoxide and hydrogen yet be able to protect the fermentation from adverse components despite changes in biomass feedstock and changes in gasifier performance.

SUMMARY OF THE INVENTION

In accordance with this invention processes are provided for the conversion of biomass to oxygenated organic compound using a simplified syngas cleanup operation that is cost effective and protects the fermentation operation. The processes of this invention treat the crude syngas from the gasifier by non-catalytic partial oxidation. The partial oxidation provides several advantages beyond reducing the hydrocarbon content such as methane, ethylene and acetylene contained in the crude syngas. Namely, the partial oxidation increases the concentration of both hydrogen and carbon monoxide and lowers the hydrogen to carbon monoxide mole ratio which is particularly advantageous in producing syngas for anaerobic fermentation. The partial oxidation generally results in a reverse water gas shift being observed such that the carbon dioxide concentration is decreased. Accordingly, a higher percentage of the biomass becomes available for bioconversion to oxygenated organic compound.

Also, the partial oxidation materially reduces the concentration of other components that may adversely affect the fermentation. These components include nitric oxide, nitrogen dioxide, and hydrogen cyanide. The reduction of the hydrocarbons and other components may be sufficient such that little, if any further clean-up treatment is required. Even if further clean-up treatment is required, the concentration of components such as alkenes, alkynes and light aromatics such as benzene, toluene, xylene and naphthalene along with heavy tars, is so reduced by the partial oxidation that the process operation need only remove a small amount of these components. Importantly, the concentrations of these components generally fall within a small range even though their concentrations in the crude syngas may vary widely due to variations in gasifier performance and in biomass.

The partial oxidation in accordance with the processes of this invention is conducted without the need for sulfur compound removal operations in advance of the partial oxidation, e.g., for the removal of hydrogen sulfide, carbonyl sulfide and organosulfur compounds such as mercaptans.

The broad aspect of the processes of this invention for continuously converting biomass into oxygenated organic compound comprise:

(a) continuously gasifying biomass at elevated temperature to provide a crude syngas at a temperature of at least about 450° C., said crude syngas having a Component Composition containing carbon monoxide, hydrogen, and carbon dioxide and at least about 3, sometimes at least about 5, say, 5 to 15, mole percent methane; at least about 100 ppm (mole) hydrogen sulfide, at least about 600, sometimes at least about 1000, say 1000 to 7000, ppm (mole) benzene, at least about 1000, sometimes at least about 2000, say, 2500 to 12,000, ppm (mole) ethylene, at least about 500 ppm (mole) acetylene, at least about 20, often at least about 25 to 50, ppm (mole) hydrogen cyanide, and ash;

(b) removing by phase separation a major portion by mass of the ash while the crude syngas is maintained at a temperature of at least about 350° C. to provide an ash-reduced crude syngas;

(c) continuously contacting the ash-reduced crude syngas with oxygen-containing gas under partial oxidation conditions to perform a partial oxidation at a temperature of between about 800° C. to 1700° C., preferably 1150° C. to 1500° C., and for a time sufficient to provide a partially-oxidized syngas having a Component Composition containing less than about 1, preferably between about 0.1 and 0.75, and often between about 0.1 and 0.4, mole percent methane and at least the same molar concentration of carbon monoxide as contained in the ash-reduced crude syngas on a Component Composition basis, said partially-oxidized syngas having a Component Composition containing at least about 80 ppm (mole) hydrogen sulfide, less than 200 ppm (mole) ethylene, less than 100 ppm (mole) acetylene;

(d) continuously cooling the partially-oxidized syngas at least partially by contact with water to cool the partially-oxidized syngas to a temperature below about 100° C., preferably below about 50° C., and provide a quenched syngas containing less than about 80 ppm (mole) hydrogen sulfide on a Component Composition basis; and (e) removing hydrogen cyanide from the quenched syngas by at least one of sorption and chemical reaction to provide a fermentation gas feed with a Component Composition having a hydrogen cyanide content of less than about 2, preferably less than about 0.5, ppm (mole); and (f) continuously supplying the gas feed to a fermentation zone having an aqueous menstruum containing microorganisms suitable for converting syngas to oxygenated organic compound, said aqueous menstruum being maintained under anaerobic fermentation conditions, to produce said oxygenated organic compound.

The gasification of step (a) may be a direct, indirect or partially direct gasification. An indirect gasification does not use free oxygen, but an external source of heat is required. Direct gasification occurs where a oxygen is used to partially oxidize the biomass. Where the gasifying of step (a) is conducted in a direct or partially direct mode, the crude syngas often has a Component Composition containing at least about 50 ppm (mole) nitric oxide. Where the gasifying of step (a) is conducted in an indirect mode, i.e., heat for the gasification is indirectly supplied, the nitric oxide content of the Component Composition of the crude syngas is typically less than about 5 ppm (mole). In the preferred processes of this invention, the gasification is conducted by supplying the heat for gasification at least partially in an indirect mode.

Preferably the partial oxidation of the crude syngas in step (c) is non-catalytic. The oxygen-containing gas for the partial oxidation may be air or air enriched with oxygen. Where the partial oxidation is conducted using oxygen enriched air or oxygen, the oxygen-containing gas has a Component Composition having an oxygen content of at least about 50, preferably at least about 90, and most preferably at least about 98, mole percent oxygen. The presence of nitrogen in the oxygen-containing gas can led to the production of nitric oxide. Where air is used as the oxygen-containing gas, the nitric oxide concentration of the Component Composition of the treated syngas may be as high as 1000 ppm (mole). With oxygen-enriched oxygen-containing gas, the nitric oxide concentration in the partially oxidized syngas Component Composition may be in the range of 0.1 to 100 ppm (mole). The partial oxidation may be conducted by at least one of directly contacting the crude syngas with oxygen-containing gas and by admixing a fuel with oxygen-containing gas prior to contacting with the crude syngas. In the latter case, preferably the fuel is partially combusted to provide heat and an oxygen-containing mixture. The heat raises the temperature of the fuel and oxygen-containing mixture to desired temperatures for the partial oxidation and may also be used in indirect heat exchange with the crude syngas to increase its temperature.

A further aspect of this invention is a continuous process for the partial combustion of crude syngas having a Component Composition containing at least about 3 mole percent methane comprising:
  (a) continuously contacting a stream containing crude syngas with an oxygen-containing stream under partial oxidation conditions including a temperature of between about 800° C. to 1700° C., preferably 1150° C. and 1500° C., and a rate of supply of said oxygen-containing stream sufficient to perform a partial oxidation to provide a partially-oxidized syngas;
  (b) determining the methane content in the partially-oxidized syngas; and
  (c) adjusting the rate of supply of the oxygen-containing stream such that the partial oxidation conditions provide a partially-oxidized syngas having a Component Composition containing between about 0.1 and 0.75, preferably between about 0.1 and 0.4, mole percent methane.

In a preferred embodiment of this aspect of the invention, the oxygen-containing stream is a mixture of hydrocarbon fuel and oxygen-containing gas and the mole ratio of hydrocarbon fuel and oxygen-containing gas is also adjusted to provide a partially-oxidized syngas having a Component Composition containing between about 0.1 and 0.75, preferably between about 0.1 and 0.4, mole percent methane. In some instances, the hydrocarbon fuel and oxygen-containing gas is partially combusted prior to contacting the stream containing crude syngas. The partial combustion provides heat and an oxygen-containing mixture. The heat raises the temperature of the oxygen-containing mixture to desired temperatures for the partial oxidation and may also be used in indirect heat exchange with the crude syngas to increase its temperature.

A further aspect of this invention pertains to partially-oxidized syngas compositions. The processes of this invention provide compositions upon partial oxidation of the crude syngas having a Component Composition comprising:
  (a) hydrogen and carbon monoxide wherein the mole ratio of hydrogen to carbon monoxide is between about 0.4:1 to 1.5:1, preferably between about 0.8:1 and 1.3:1, and wherein hydrogen and carbon monoxide comprise at least about 70, preferably at least about 75, and most preferably at least about 80, mole percent of the syngas composition;
  (b) between about 0.1 and 0.75, preferably between about 0.1 and 0.4, mole percent methane;
  (c) between about 1 and 100, preferably between about 1 and 30, ppm (mole) acetylene;
  (d) between about 10 and 200, preferably between about 10 and 70, ppm (mole) ethylene;
  (e) between about 0.1 and 50, say, 0.5 to 20, ppm (mole) hydrogen cyanide; and
  (f) between about 2 and 25, preferably between about 5 and 15, mole percent carbon dioxide.

In a further aspect of this invention the partially-oxidized syngas composition also undergoes cleaning that provides a partially-oxidized and cleaned syngas having a Component Composition comprising:
  (a) hydrogen and carbon monoxide wherein the mole ratio of hydrogen to carbon monoxide is between about 0.4:1 to 1.5:1 and wherein hydrogen and carbon monoxide comprise at least about 70 mole percent of the syngas composition;
  (b) between about 0.1 and 1.0 mole percent methane;
  (c) between about 0.1 and 100 ppm (mole) acetylene
  (d) between about 0.1 and 50 ppm (mole) ethylene;
  (e) between about 0.001 and 2 ppm (mole) hydrogen cyanide; and
  (f) between about 1 and 20 mole percent carbon dioxide.

The syngas will contain water and nitrogen. The amount of nitrogen will, in part, depend upon the composition of the feedstock, nature of the gasification process, and the oxygen-containing gas used for the partial oxidation. Where an indirect gasification process is used and partial oxidation is conducted using an oxygen-containing gas having a high molecular oxygen content, the nitrogen content can be relative low, say, from about 0.1 to 5 mole percent of the Component Composition of the syngas. Direct gasification processes using air and partial oxidation processes using air, can yield a syngas Component Composition with nitrogen concentrations as high as 55 to 60 mole percent of the syngas. The preferred syngas Component Compositions contain at least about 20, often between about 80 and 300, ppm (mole) hydrogen sulfide and contain between about 2 and 100, more frequently between about 3 and 50, say, 3 to 30, ppm (mole) benzene. The syngas Component Composition usually contains other components such as tars such as naphthalene and heavier aromatics (generally less than about 500, preferably less than about 150, ppm (mole)), lighter aromatics other than benzene such as toluene and xylene (often between about 2 and 70 ppm (mole)), carbonyl sulfide (often between 0.1 and 25 ppm (mole)), and ammonia (often between about 100 and 10,000 ppm (mole)).

Another aspect of this invention pertains to apparatus for the conversion of biomass to oxygenated product comprising:
  (a) at least one gasifier capable of converting biomass to syngas at a temperature of at least about 450° C. having at least one biomass input port and at least one syngas exit port;
  (b) at least one solids removal device capable of operating at least at 350° C. in fluid communication with at least one syngas exit port of a gasifier and capable of removing solids from syngas;

(c) at least one partial oxidation unit having at least one crude syngas inlet port, at least one oxygen inlet port and at least one partially-oxidized syngas exit port, said crude syngas inlet port being in fluid communication with at least one solids removal device, and said at least one oxygen inlet port being in fluid communication with a source of an oxygen-containing gas;

(d) at least one methane detector in fluid communication with at least one partially-oxidized syngas exit port capable of determining the concentration of methane in the gas passing through the at least one partially-oxidized syngas exit port and generating a control signal corresponding to such concentration;

(e) a controllable valve positioned between the source of an oxygen-containing gas and the at least one oxygen inlet port that is controlled in response to the control signal from the at least one methane detector;

(f) at least one heat exchanger in fluid communication with at least one partially-oxidized syngas exit port adapted to contact gas from the at least one partial oxidation unit with aqueous medium to provide a cooled gas at a temperature less than about 100° C., preferably less than about 50° C., at a cooled gas exit port, at least one of said heat exchangers adapted to provide direct contact of the partially-oxidized syngas with water;

(g) at least one hydrogen cyanide removal unit in fluid communication with the cooled gas exit port adapted to provide at one or more treated exit ports a hydrogen cyanide depleted gas;

(h) at least one fermentor in fluid communication with the at least one treated exit port, said fermentor containing an aqueous menstruum under anaerobic fermentation conditions, said aqueous menstruum comprising microorganisms suitable for converting carbon monoxide and hydrogen and carbon dioxide to oxygenated organic compound, said fermentor comprising at least one gas exit port and at least one liquid exit port; and (i) at least one oxygenated organic compound recovery unit in fluid communication with the at least one liquid exit port adapted to recover oxygenated organic compound from said aqueous menstruum.

DETAILED DISCUSSION

Definitions

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

Aqueous menstruum means a liquid water phase which may contain dissolved compounds including, but not limited to hydrogen, carbon monoxide, and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

The abbreviation ppm means parts per million. Unless otherwise stated or clear from the context, ppm is on a mole basis (ppm (mole)).

Stable gas-in-liquid dispersion means a mixture of gas bubbles in liquid where (i) the bubbles predominantly flow in the same direction as the liquid, and (ii) the dispersion is sufficiently stable that it exists throughout the aqueous menstruum, i.e., insufficient coalescing of bubbles occurs to destroy the dispersion.

For a syngas to oxygenated organic compound fermentation process to be commercially viable, capital and operating costs must be sufficiently low that it is at least competitive with alternative biomass to oxygenated organic compound processes. For instance, ethanol is commercially produced from corn in facilities having name plate capacities of over 100 million gallons per year. Accordingly, the syngas to oxygenated organic compound fermentation process must be able to take advantage of similar economies of scale. Thus, a commercial scale facility may require at least 20 million liters of fermentation reactor capacity.

Overview

The processes of this invention pertain to the conversion of biomass to oxygenated organic compound by gasification to provide a substrate containing carbon monoxide, hydrogen and carbon dioxide and bioconversion of the substrate to the oxygenated organic compound via anaerobic fermentation.

Biomass Gasification

Gasification is a thermal process to convert biomass. The gasification may be effected by any suitable process to provide a gas containing carbon monoxide and hydrogen and may involve the presence of controlled amounts of oxygen and steam. Typically gasification involves heating the biomass in an oxygen-controlled environment. The heat may be provided by direct or indirect heat exchange as stated above. Various types of gasifiers include pyrolysis, counter current fixed bed, co-current fixed bed, moving bed, fluidized bed, entrained flow and plasma gasifiers. One type of gasification process is the Taylor gasification process generally disclosed in United States published patent application No. 2008024496 A1, hereby incorporated by reference in its entirety. The process may involve a combination of pyrolysis and steam reforming. In accordance with this invention, gasification occurs at a temperature of at least about 450° C., often between about 500° C. and 1500° C., say, 600° C. to 1250° C. The gasification may be conducted at any suitable pressure including subatmospheric pressure, but is typically conducted at pressures from about 100 to 5000 KPa absolute.

Typically the biomass is pre-conditioned prior to gasification, for instance by communition to provide biomass of suitable size for the gasification process used and by drying to provide a moisture content of less than about 30 mass percent, often in the range of about 5 to 20 mass percent. Maintaining a relatively constant moisture content of the biomass facilitates control of the gasification process. Usually energy from the conversion process is recovered to provide heat for the drying in order to enhance overall efficiency of the process to make oxygenated organic compound. Where biomass to be fed has high moisture content, such as municipal waste, admixture with another, drier biomass may facilitate handling and reduce the amount of energy required to achieve the sought moisture content for the biomass feed. If desired, the biomass being fed to the gasifier can be contacted with the crude gas stream from the gasifier to heat, and in some instances, initiate pyrolysis of at least a portion of the biomass feed. Advantageously, if such a step is used, the crude syngas is not cooled below about 350° C.

Gasification of biomass, however, leads to the formation of a complex set of by-products due to the nature of the biomass constituents and the conditions of the gasification. These by-products include tars, char and ash, light hydrocarbons, nitrogen oxides, other nitrogenous compounds such as hydrogen cyanide and sulfur compounds. To some extent, the formation of by-products can be affected by the conditions of the gasification as is known in the art. Lower gasification temperatures generally tend to increase the content of tars and lighter hydrocarbons. Higher gasification temperatures generally tend to increase operating and capital costs. Table I provides typical crude syngas Component Compositions that are produced by some available gasification unit operations.

TABLE I

| Component | Minimum | Maximum | Preferred Minimum | Preferred Maximum |
|---|---|---|---|---|
| Carbon Monoxide, mole % | 20 | 60 | 30 | 60 |
| Hydrogen, mole % | 20 | 60 | 30 | 60 |
| Carbon Dioxide, mole % | 5 | 35 | 10 | 25 |
| Methane, mole % | 3 | 15 | 3 | 12 |
| Acetylene, ppm (mole) | 40 | 2500 | 200 | 2000 |
| Ethylene, ppm (mole) | 400 | 25000 | 1000 | 12000 |
| Benzene, ppm (mole) | 600 | 10000 | 1000 | 7500 |
| Tars, naphthalene, ppm (mole) | 100 | 10000 | 200 | 5000 |
| Hydrogen sulfide, ppm (mole) | 80 | 1000 | 80 | 500 |
| Carbonyl sulfide, ppm (mole) | 3 | 100 | 5 | 50 |
| Ammonia, ppm (mole) | 100 | 10000 | 500 | 7500 |
| Nitric oxide, ppm (mole) | 0.5 | 1000 | 1 | 500 |
| Hydrogen cyanide, ppm (mole) | 20 | 100 | 20 | 50 |
| Other, ppm (mole) | 100 | 100000 | 200 | 20000 |

(Not including water and nitrogen)

Solids Removal

Gasification of biomass results in the formation of ash (including char). The amount of these solids present in the crude syngas will depend not only upon the type of gasifier used but also the nature of the biomass. In accordance with the processes of this invention, the crude syngas from the gasifier is maintained at a temperature of at least about 350° C., preferably at least about 500° C. or 600° C., and sometimes in the range of about 700° C. to 1500° C. This provides several advantages. First, equipment required to further cool the crude syngas is not required resulting in a capital cost savings. Second, as the gasification process is conducted at an elevated temperature, heat required to increase the temperature of the crude syngas is reduced. Third, higher boiling hydrocarbon containing components that are capable of being partially-oxidized to form carbon monoxide and hydrogen are maintained in the gas phase. And fourth, maintaining the crude syngas at these high temperatures reduces the formation of waxy deposits on the piping and equipment.

However, gasification of biomass results in the formation of ash (including char) and at least some of the ash will be entrained in the crude syngas. The amount of these solids present in the crude syngas will depend not only upon the type of gasifier used but also the nature of the biomass. The processes of this invention comprise removing at least about 75, preferably at least about 90 to essentially 100, mass percent of the solids from the crude syngas. The removal of solids can be effected in any suitable manner. Cyclones are preferred since in most instances, cyclones are capable of removing sufficient entrained solids.

The solids removed from the crude syngas and any solids removed from the gasifier usually contain non-volatilized tars. If desired, additional heat and syngas values can be recovered by subjecting these solids to oxidation conditions preferably including temperatures of at least about 700° C. and the presence of oxygen-containing gas such as air especially where heating values are sought, or oxygen or oxygen enriched air where additional syngas is sought to be produced without undue nitrogen content.

Partial Oxidation

The partial oxidation step of this invention benefits from having a crude syngas feed that is already at an elevated temperature, i.e., at a temperature of at least about 350° C. The partial oxidation may be conducted in any suitable manner to effect a reduction in methane content of the syngas Component Composition to less than about 1, preferably between about 0.1 and 0.75, often between about 0.1 and 0.4, mole percent. As stated above, other components of the syngas such as other hydrocarbons, nitrogen oxides, and hydrogen cyanide, are also affected by the partial oxidation conditions that provide the reduction of methane content. Accordingly, a partially-oxidized syngas is produced that may require little, if any, further cleanup treatment to be a satisfactory gas feed for anaerobic fermentation to produce oxygenated organic compound.

Since the crude syngas contains sulfur compounds, the partial oxidation is preferably conducted in a non-catalytic manner. The partial oxidation is typically conducted at a temperature in the range of between about 800° C. to 1700° C., say, 1150° C. and 1500° C., preferably about 1250° C. and 1500° C. Generally the partial oxidation is substantially adiabatic, and thus the targeted temperature will be achieved by a combination of the temperatures, duration of the partial oxidation and relative mass flow rates of the input gases and the heat generated by the partial oxidation. All else being substantially the same, lower partial oxidation temperatures tend to result in higher methane concentrations in the partially-oxidized syngas and higher partial oxidation temperatures tend to result in higher carbon dioxide concentrations in the partially-oxidized syngas. While not intending to be limited to theory, it is believed that the generation of free radicals play a role in the partial oxidation of the crude syngas. Where the crude syngas contains free radical inhibitors such as halides, it may be desirable to use higher temperatures for the partial oxidation. The partial oxidation may be conducted at subatmospheric, atmospheric or superatmospheric pressure. Typically the pressure used for the partial oxidation is in the range of between about 100 and 3000, preferably between about 100 and 500, KPa absolute. The conditions of the partial oxidation are preferably such that combustion is avoided or mitigated. Often the velocity of the total gases during partial oxidation is sufficiently high to avoid a flame front, for instance, at least about 150, preferably at least about 200, say, between about 250 and 500, meters per second. At these partial oxidation conditions, the partial oxidation can be conducted relatively rapidly.

Oxygen-containing gas is admixed with the crude syngas for purposes of the partial oxidation. The source of the oxygen may be air, oxygen-enriched air or substantially pure oxygen. Where it is desired to avoid undue nitrogen dilution of the syngas, the source of the oxygen for the oxygen-containing gas preferably contains at least about 75, preferably at least about 90, and most preferably at least about 98, mole percent oxygen (concentration including the presence of nitrogen but is on an anhydrous basis). The oxygen-containing gas prior to contacting the crude syngas may contain components other than oxygen and nitrogen, including, but not limited to, hydrogen, carbon monoxide, carbon dioxide, hydrocarbon-containing compounds (preferably hydrocarbon-containing compounds having between about 1 and 20 carbons), and water vapor. The amount of oxygen provided is sufficient to provide the sought partial oxidation temperature and reduction of methane in the treated syngas. The amount of oxygen required for a specific crude syngas composition will depend upon the composition of the syngas, whether or not any additional fuel is provided for the partial oxidation, the concentration of methane and additional fuel in the crude syngas composition and the extent the methane and any additional fuel is desired to be converted into incrementally additional syngas. In general, the mass ratio of oxygen to total methane and any added hydrocarbon fuel is between about 0.3:1 to 3.5:1.

As stated above, one convenient method for effecting the partial oxidation of the crude syngas with conservation of carbon monoxide and hydrogen values comprises adding a hydrocarbon-containing fuel to the crude syngas. The terms "hydrocarbon-containing fuel" and "fuel" as used herein refer to fuels that contain hydrogen and oxygen atoms and may contain hetero atoms including, but not limited to oxygen and nitrogen atoms. Typically hydrocarbon-containing fuels are less expensive than syngas. Combustion of the fuel provides heat to provide the sought partial oxidation temperature. Hydrocarbon-containing fuels include, but are not limited to, natural gas, propane, liquified petroleum gas, butane, fuel oil, petroleum fractions having normal boiling points between about 35° C. and 350° C., and oxygenated hydrocarbons such as alkanols (such as methanol, ethanol, propanol, and butanol) diols (such as ethylene glycol), esters, ethers, and carboxylic acids of 1 to 20 carbons. The amount of fuel added will, in part, depend upon the amount of heat necessary to be generated to achieve the sought partial oxidation temperature. More hydrocarbon-containing fuel can be added, and its partial oxidation will result in the production of additional syngas. Often, the amount of hydrocarbon-containing fuel added is at least about 0.5, say, at least about 1, and sometimes between about 1 and 10, for instance, 1 and 5, mass percent of the crude syngas on a Component Composition basis.

The fuel may be added before combustion to the crude syngas, or may be partially or substantially fully combusted when added to the syngas to effect the partial oxidation of the crude syngas. Preferably the fuel is in admixture (fuel/oxygen admixture) with oxygen before combination with the crude syngas, that is, the fuel and oxygen from the source of oxygen is the oxygen-containing gas. In some instances, a portion of the fuel/oxygen admixture is partially combusted prior to admixture with the syngas (pre-reaction). Frequently, the pre-reaction of the fuel/oxygen admixture consumes from about 80 or 90 to essentially 100 mass percent of the fuel. The pre-reaction may be under the same or different conditions than those for the partial oxidation of the syngas. The pre-reaction may be catalytic or non-catalytic. The pre-reaction serves to increase the temperature of the fuel/oxygen admixture and can be used to increase the temperature of the crude syngas by direct or indirect heat exchange. Examples of types of apparatus for providing and pre-reacting the fuel/oxygen admixture are disclosed in U.S. Pat. Nos. 5,266,024 and 6,471,937, both herein incorporated by reference in their entireties.

One or more partial oxidation zones may be used to effect the partial oxidation of the syngas. Parallel oxidation zones facilitate start-up and turn down operations as the volume of crude syngas changes substantially. Sequential partial oxidation zones can also be used to facilitate start-up and turn down operations with a sequential partial oxidation zone either being taken off line or put on line or with the flow of oxygen-containing gas to a partial oxidation zone being changed in response to the change in crude syngas flow. Each partial oxidation zone may have one or more ports for the introduction of each of the crude syngas and the oxygen-containing gas. A partial oxidation zone may comprise a static mixer to facilitate mixing of the crude syngas and the oxygen-containing gas. Where the crude syngas being passed to the partial oxidation zone is at a temperature below that desired, the partially-oxidized syngas from that or another partial oxidation zone may be used in indirect heat exchange to increase the temperature of the feed and cool the partially-oxidized syngas.

Preferably the partial oxidation conditions are selected to adjust the hydrogen to carbon monoxide mole ratio and to decrease the concentration of carbon dioxide in the syngas. In part, these results are obtained by a reverse water gas shift. In general, partial oxidation conditions wherein higher input hydrocarbon (from the crude syngas and potentially the added hydrocarbon fuel) is increased, higher hydrogen to carbon monoxide ratios are obtained, all else being maintained substantially constant. The mole ratio of hydrogen to carbon monoxide in the partially-oxidized syngas is often between about 0.4:1 to 1.5:1, preferably between about 0.8:1 and 1.3:1. For many anaerobic fermentation microorganisms, carbon monoxide is a preferred substrate for bioconversion to oxygenated organic compound. Moreover, the partial oxidation provides a net increase in this substrate not only because of the conversion of hydrocarbons but also due to the reverse water gas shift. The Component Composition of the partially-oxidized syngas frequently has the compositions set forth in Table II.

TABLE II

| Component | Minimum | Maximum | Preferred Minimum | Preferred Maximum |
|---|---|---|---|---|
| Carbon Monoxide, mole % | 25 | 65 | 35 | 60 |
| Hydrogen, mole % | 25 | 65 | 35 | 60 |
| Carbon Dioxide, mole % | 3 | 30 | 5 | 20 |
| Methane, mole % | 0.1 | 1 | 0.1 | 0.75 |
| Acetylene, ppm (mole) | 1 | 100 | 1 | 30 |
| Ethylene, ppm (mole) | 10 | 200 | 10 | 70 |

TABLE II-continued

| Component | Minimum | Maximum | Preferred Minimum | Preferred Maximum |
|---|---|---|---|---|
| Benzene, ppm (mole) | 2 | 100 | 3 | 30 |
| Tars, naphthalene, ppm (mole) | 1 | 500 | 1 | 100 |
| Hydrogen sulfide, ppm (mole) | 20 | 300 | 80 | 300 |
| Carbonyl sulfide, ppm (mole) | 0.1 | 25 | 0.5 | 20 |
| Ammonia, ppm (mole) | 10 | 10000 | 10 | 7500 |
| Nitric oxide, ppm (mole) | 0.5 | 1000 | 0.5 | 50 |
| Hydrogen cyanide, ppm (mole) | 0.1 | 50 | 2 | 30 |
| Other, ppm (mole) | 100 | 10000 | 20 | 10000 |

(Excluding nitrogen and water)

As can be seen from Table II, the partial oxidation substantially attenuates the concentration of numerous components in the crude syngas thereby facilitating any further desired removal of such components from the syngas prior to introduction into the fermentation menstruum.

An aspect of this invention pertains to processes for the partial oxidation of a crude syngas where the rate of supply of the oxygen-containing stream to the partial oxidation step is adjusted to achieve a targeted methane concentration in the partially-oxidized syngas. By this invention it has been found that at methane concentrations above about 0.75 or 1 mole percent on a Component Composition basis, the partial oxidation conditions are not sufficiently severe to effect the sought reduction of acetylene, ethylene and other components that can adversely affect many microorganisms suitable for anaerobic fermentation of syngas to oxygenated organic compound. However, if the partial oxidation conditions are too severe, i.e., the methane concentration in the partially-oxidized syngas falls below about 0.1 mole percent on a Component Composition basis, undue loss of carbon monoxide and hydrogen tends to occur. In many operations, it is desired to control the partial oxidation to achieve about 0.1 to 0.4 mole percent methane on a Component Composition basis in the partially-oxidized syngas. Where a fuel is added to the crude syngas during partial oxidation, the rate of fuel supply is an additional variable that can be used to adjust the temperature of the partial oxidation and the concentration of methane in the partially-oxidized syngas. The temperature of the partial oxidation is also affected by the rate of supply of oxygen-containing gas.

Syngas Cooling

The partially-oxidized syngas is promptly cooled upon exiting the partial oxidation operation. The cooling may involve one or more unit operations. Advantageously due to the high temperature of the partially-oxidized syngas, heat in the syngas is recovered in a steam boiler to provide steam supply for the biomass conversion process. Preferably, the steam generated is at a pressure of between about 750 and 1500, say, 900 to 1100, KPa absolute and the temperature of the partially-oxidized syngas is reduced to between about 120° C. to 180° C. Alternatively, or in addition, the partially-oxidized syngas may be used in indirect heat exchange with other process streams such as the crude syngas passing to the partial oxidation or to heat air used to dry biomass.

The cooling in accordance with the processes of this invention involves at least one direct heat exchange with water. Usually this direct heat exchange occurs only after the partially-oxidized syngas has been cooled to a temperature below about 180° C., preferably below about 150° C. The direct heat exchange may involve passing the syngas through water or a countercurrent contact with a water spray, and the syngas is cooled to a temperature below about 100° C., preferably below about 50° C., and often at a temperature suitable for introduction into a fermentor or for any optional cleanup operation.

The direct heat exchange also serves to remove a portion of hydrogen sulfide, ammonia and at least some of the hydrogen cyanide contained in the partially-oxidized syngas. The amount of hydrogen cyanide removed can be enhanced by maintaining the cooling water at a pH in the range of about 5.5 to 8, say, about 6 to 6.5. Additionally, reactants for hydrogen cyanide such as acetaldehyde can me contained in the cooling water. Accordingly, the direct heat exchange with water can also serve to remove hydrogen cyanide to levels suitable such that the cooled syngas can be introduced into the fermentation operation without further cleanup treatment.

Optional Cleanup

Subsequent to the cooling of the syngas, in some instances additional cleanup of the syngas may be desired. The additional cleanup may be desired because of the sensitivity of the particular microorganisms used for the anaerobic fermentation to the residual amounts of one or more of the components in the syngas. Where the operation of the partial oxidation is primarily sought to lower the concentration of components sought to be removed as opposed to reducing them to levels tolerable in the fermentation, additional cleanup will be required. As stated above, the lowering of the concentration of these components facilitates the removal of these components in subsequent cleanup operations. More importantly, even with wide variations in concentrations of these components in the crude syngas, the variations in concentration of the syngas after partial oxidation are attenuated. Hence the equipment design and control systems need not address the wide variations.

One optional cleanup operation is water scrubbing. Hydrogen cyanide can be removed by water scrubbing or by scrubbing in the presence of a reactant. See, for instance, United States Published Patent Application No. 20110097701 A1, hereby incorporated by reference in its entirety. The water scrubbing also serves to remove at least a portion of remaining impurities from the syngas such as ethylene, acetylene, ammonia, hydrogen sulfide and carbonyl sulfide. The scrubbing may be conducted in any convenient manner. Often, the temperature of the scrubbing is in the range of about 4° C. to 50° C., and the scrubbing may be conducted at subatmospheric, atmospheric or superatmospheric pressure, e.g., frequently at about 105 to 1000 KPa absolute. Water pressure swing absorption can be used if desired. The pH of the scrubbing solution is usually maintained in the range of about 5.5 to 8, preferably between about 6 to 6.5. Reactants for hydrogen cyanide can be advantageous in that hydrogen cyanide can be converted to less toxic compounds. Aldehydes are particularly preferred reactants due to their availability. Examples of aldehydes include, but are not limited to, formaldehyde, acetaldehyde, and acrolein(prop-2-enal) with formaldehyde being most preferred.

Another optional cleanup operation is chemical oxidation with one or more peroxygenated reactants, preferably permanganate such as sodium permanganate and potassium permanganate. The chemical oxidation is particularly effective in reducing the concentration of compounds that have ethylenic and acetylenic unsaturation and reducing the concentration of nitric oxide and sulfur compounds. The chemical oxidation may be conducted using the peroxygenated reactant in an aqueous solution. Often, the temperature of the chemical oxidation is in the range of about 4° C. to 50° C., and the chemical oxidation may be conducted at subatmospheric, atmospheric or superatmospheric pressure, e.g., frequently at about 105 to 1000 KPa absolute. The pH of the chemical oxidation solution is usually maintained in the range of about 5.5 to 8, preferably between about 6 to 6.5.

Another cleanup operation uses chemical scavengers such as sodium hydroxide, nitric acid, sodium hypochlorite and the like in an aqueous scrubbing solution to remove one or more components from the syngas. If a chemical oxidation is used, this type of cleanup operation is usually unnecessary.

Carbon dioxide can be removed from the syngas. In most instances, the concentration of carbon dioxide in the partially-oxidized syngas is sufficiently low that a carbon dioxide removal operation is not necessary to achieve acceptable fermentation performance. However, if off gases from the fermentation are recycled, it is possible that undesirable carbon dioxide build-up could occur. In such instances, a carbon dioxide removal step could be justified during the cleanup of the syngas especially where no carbon dioxide is being removed from the recycling off gases. Any suitable carbon dioxide removal process may be used including amine extraction, alkaline salt extractions, water absorption, membrane separation, adsorptions/desorption, and physical absorption in organic solvents. A preferred process for removal of carbon dioxide from gases is by contacting the gas with an aqueous solution containing oxygenated organic compound. This process is disclosed in U.S. Patent application No. 2008/0305539, filed Jul. 23, 2007, herein incorporated by reference in its entirety. See also, U.S. patent application Ser. No. 12/826,991, filed Jun. 30, 2010 herein incorporated by reference in its entirety, which discloses contacting a gas stream with a mixture of water and a surface active agent under pressure to sorb carbon dioxide and phase separating the gas and liquid stream to provide a gas stream with reduced carbon dioxide concentration to be used as feed to a reactor.

Another optional cleanup operation comprises contacting the syngas with aqueous fermentation medium containing microorganisms being discharged from the fermentation operation, said contacting being under anaerobic fermentation conditions. Components such as hydrogen cyanide and acetylene that are absorbed by the microorganism but are not released or not readily released can thus be removed with the microorganisms from the syngas prior to being introduced into the fermentation operation. The contacting may be by any suitable manner provided that sufficient residence time of the gas phase exists for mass transfer of the components sought to be removed to the aqueous phase. Apparatus such as bubble column reactors; jet loop reactors; stirred tank reactors; trickle bed reactors; biofilm reactors; and static mixer reactors including, but not limited to, pipe reactors may find application for this cleanup operation. Oxygenated organic compound is usually produced and can be recovered from the aqueous phase. A discussion of pre-reactors is provided in copending U.S. patent application Ser. No. 13/243,347, filed on Sep. 23, 2011, hereby incorporated in its entirety by reference.

Fermentation Gas Feed

The cleaned syngas serves as fresh gas feed to the fermentation operation. The cleaned syngas may be admixed with other gases, including but not limited to, syngas from other sources and recycled off gas from the fermentation. The syngas from other sources may include, but is not limited to, syngas from another biomass gasifier, syngas made from other sources of hydrocarbon such as natural gas, gas generated by reforming or partial oxidation of hydrocarbon-containing materials, and gas generated during petroleum and petrochemical processing. Thus, the gas feed to a fermentor may have the same or a different composition as the composition of the cleaned syngas. The composition of the syngas generated from biomass may be processed to provide a composition which, when admixed with the gases from the other sources, is suitable for a gas feed to the fermentation operation. The Component Composition of typical cleaned syngas is set forth in Table III.

TABLE III

| Component | Minimum | Maximum | Preferred Minimum | Preferred Maximum |
|---|---|---|---|---|
| Carbon Monoxide, mole % | 25 | 70 | 40 | 65 |
| Hydrogen, mole % | 30 | 70 | 40 | 65 |
| Carbon Dioxide, mole % | 1 | 20 | 3 | 15 |
| Methane, mole % | 0.1 | 1 | 0.1 | 0.75 |
| Acetylene, ppm (mole) | 0.1 | 10 | 1 | 5 |
| Ethylene, ppm (mole) | 0.1 | 50 | 0.5 | 10 |
| Benzene, ppm (mole) | 0.001 | 30 | 0.05 | 10 |
| Tars, naphthalene, ppm (mole) | 0.001 | 10 | 0.001 | 5 |
| Hydrogen sulfide, ppm (mole) | 0.01 | 30 | 0.05 | 20 |
| Carbonyl sulfide, ppm (mole) | 0.01 | 25 | 0.05 | 15 |
| Ammonia, ppm (mole) | 0.5 | 1000 | 1 | 750 |
| Nitric oxide, ppm (mole) | 0.5 | 100 | 0.5 | 50 |
| Hydrogen cyanide, ppm (mole) | 0.001 | 2 | 0.001 | 0.3 |
| Other, ppm (mole) | 100 | 10000 | 20 | 10000 |

(Excluding nitrogen and water)

Oxygenated Compound, Microorganisms and Fermentation Conditions:

The oxygenated organic compounds produced in the processes of this invention will depend upon the microorganism used for the fermentation and the conditions of the fermentation. One or more microorganisms may be used in the fermentation menstruum to produce the sought oxygenated organic compound. Bioconversions of CO and $H_2/CO_2$ to acetic acid, propanol, butanol, butyric acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Suitable microorganisms for bioconversion of syngas to oxygenated organic compound generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation reactor and its operation. The pressure may be subatmospheric, atmospheric or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous menstruum for the fermentation, the pressure will vary within the fermentation reactor based upon the static head.

The fermentation conditions are preferably sufficient to effect at least about 40 or 50 percent conversion of the carbon monoxide in gas feed. For commercial operations, the fermentation operation preferably provides a total molar conversion of hydrogen and carbon monoxide in the net gas feed in the range of about 85 to 95 percent. Due to the low solubilities of carbon monoxide and hydrogen in the aqueous phase, achieving these high conversions may require one or more of using multiple fermentation reactors and recycling off gas from a reactor.

The rate of supply of the gas feed under steady state conditions to a fermentation reactor is such that the rate of transfer of carbon monoxide and hydrogen to the liquid phase matches the rate that carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

To increase the conversion of carbon monoxide and hydrogen in the fresh gas feed to the fermentation, off-gas withdrawn from a fermentation reactor may be recycled or passed to a fermentation reactor that is sequential in gas feed flow. Where off-gas is recycled, the portion of off-gas recycled is generally selected to avoid an undue build-up of the concentration of inerts and other gases in the fermentation reactor.

Fermentation Reactors

The fermentation reactors used in this invention may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors; and static mixer reactors including, but not limited to, pipe reactors.

One preferred type of reactor design uses biofilms. Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. U.S. published patent application No. 20080305539; U.S. published patent application No. 20090035848; and U.S. published patent application No. 20080305540, all hereby incorporated by reference in their entireties, disclose membrane based bioreactors wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO and $H2/CO_2$ to ethanol and other liquid products such as butanol, acetic acid, propanol and butyric acid. In these systems the gas flows through a porous region of a hydrophobic membrane and then reaches a biofilm which is hydrophilic.

United States Published Patent Application 20090215153 A1, hereby incorporated by reference in its entirety, discloses contacting syngas components such as CO or a mixture of $CO_2$ and $H_2$ with a surface of a membrane that contains a biolayer of microorganisms and permeating liquid to and from the opposite side of the membrane will provide a stable system for producing liquid products such as ethanol, butanol, hexanol, and other chemicals. The membrane has an asymmetric construction that provides a porous side, referred to herein as a biolayer that provides pores to promote and control the growth of microorganism colonies therein while also exposing a surface over which to directly feed the microorganisms with syngas. Simultaneously another layer of the asymmetric membrane having less permeability than the biolayer, herein referred to as a hydration layer, permeates liquid from the opposite side of the asymmetric membrane. The liquid products produced in the biolayer on the membrane's gas contact side pass through the membrane and into a liquid stream that recovers the desired liquid products while also supplying nutrients to the biolayer in the reverse direction of liquid product flow.

In membrane type reactors, generally the syngas flows through the gas chamber or channels of the bioreactor system continuously or intermittently. The gas feed gas pressure is in the range of 110 to 7000 KPa absolute, preferably about 150 to 1200 KPa absolute. The differential pressure between the liquid and gas phases is managed in a manner that the membrane integrity is not compromised (e.g., the burst strength of the membrane is not exceeded) and the desired gas-liquid interface phase is maintained.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semipermeable layer having a thickness of from 0.5 to 10 μm. The skinned asymmetric membrane can include an "integrally skinned" membrane prepared by using phase inversion of one polymer or a composite membrane, where a thin layer of a certain material is formed on top of a porous sublayer of a same or different material.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO, for example a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK). Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 μm, are made of polysulfone and polyvinylpyrrolidone. The BTS Highly Asymmetric Membranes, available in pore size range from 0.05 to 0.80 μm, are cast of polysulfone with a "cut off" layer of about 10 μm and a total thickness of about 120 μm. Hollow fiber membrane modules containing asymmetric ultrafiltration membranes are commercially available from a number of membrane manufacturers. For example, the KrosFlo™. Max Module Model KM5S-800-01N from Spectrum Laboratories (Rancho Dominguez, Calif.) has 22.0 $m^2$ membrane surface area of asymmetric polysulfone hollow fiber membranes with 0.5 mm fiber inner diameter, a tight skin on the lumen side, and a pore rating of 50 kDa. ROMICON™ polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 $m^2$ total membrane surface area.

Membranes of the various geometries and compositions described above may be used in arrangements of unitary arrays or assemblies of varied composition in the systems of this invention. Any suitable potting technique can be used to collect and provide the necessary assembly of individual membrane elements. In such membranes the gas and liquid can be brought into direct and intimate contact at the gas contact surface of the biolayer. Liquid is passed in the liquid side of the membranes via pumping, stirring, or similar means to remove the ethanol and other soluble products formed; the products are recovered via a variety of suitable methods.

Another preferred type of fermentation reactors for commercial scale operations are deep, tank reactors in which the microorganisms are suspended in an aqueous menstruum. Deep, tank reactors have a sufficient depth of the aqueous menstruum to increase time for mass transfer from the gas to aqueous phase and thereby enhance conversion of carbon monoxide and hydrogen. Most often deep, tank reactors are bubble column reactors, jet loop reactors and stirred tank reactors. Preferably stirred tank reactors are mechanically-assisted liquid distribution tank reactors, or MLD tank reactors where the stirring is insufficient to generate small bubbles.

Preferably the gas feed is passed through the deep, tank reactors in the form of small bubbles, sometimes microbubbles, to facilitate mass transfer of carbon monoxide and hydrogen. Microbubbles are bubbles having a diameter of 500 microns or less. The deep, tank reactor has a height of at least about 10, often between about 10 or 15 and 30, meters and an aspect ratio of height to diameter of at least about 0.5:1, say, between about 0.5:1 to 5:1, preferably between about 1:1 to 3:1.

The microbubbles of gas feed introduced into the aqueous menstruum can be generated by any suitable means including spargers and educers. Preferably they are generated by injection of the gas feed with a motive liquid. In preferred processes, the gas feed is injected into the deep, tank reactor as a relatively stable gas-in-water dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The use of injectors can provide better control over the size of the gas bubbles being introduced into the aqueous menstruum and thus the interfacial area between the gas and liquid phases. Changing bubble size thus modulates the mass transfer of carbon monoxide and hydrogen to the aqueous menstruum. Additionally, the modulation enables a microbubble size to be generated that results in a preferred, stable gas-in-water dispersion.

The motive liquid may be any suitable liquid for introduction into the reactor and often is advantageously one or more of aqueous menstruum, liquid derived from aqueous menstruum or make-up liquid to replace aqueous menstruum withdrawn from product recovery. Preferably the motive liquid comprises aqueous menstruum. The motive liquid for the injectors preferably comprises sufficient amount of one or more of oxygenated organic compound and other surface active agent to enhance the formation of microbubbles where microbubbles are sought.

In a bubble column reactor, the feed gas is introduced at the bottom of the vessel and bubbles through the aqueous menstruum. Bubble column reactors may contain axial-flow promoting devices such as baffles, down draft tubes and the like although these devices add to the capital costs of the reactors. Hence, most bubble column reactors do not contain these devices. While bubble column reactors are typically the most economical design and can provide high conversion efficiencies, other reactor designs may find utility in commercially viable bioconversion facilities. A preferred commercial scale operation using bubble columns uses sequential bubble columns to the gas feed flow. U.S. patent application Ser. No. 13/243,062, filed Sep. 23, 2011, hereby incorporated by reference in its entirety, discloses anaerobic fermentation processes using sequential deep, bubble columns to achieve high conversion of carbon monoxide and hydrogen contained in the gas feed without incurring carbon monoxide inhibition. The processes comprise the combination of (i) using at least two deep, bubble column reactors in flow series; (ii) using certain feed gas compositions; (iii) introducing the feed gas by injection with a motive liquid to produce microbubbles; and (iv) limiting the degree of conversion of carbon monoxide in the upstream reactor.

The deep, MLD tank reactors use one or more mechanical stirrers. The mechanical stirring should be sufficient to promote the uniformity of liquid composition through the reactor and need not, and preferably is not, used as a generator of a significant fraction of the microbubbles. Usually two or more mechanical stirrers are used at different heights with higher aspect ratio reactors. The design of mechanical stirrers for stirred tank reactors and their positioning within the reactors for very large diameter tanks are well within the skill of a stirred tank reactor designer. Side paddles or side mounted mixers with impellers are frequently used. Preferably the design of the mechanical stirrers and the positioning within the reactor take into consideration energy costs in generating the liquid flow to obtain uniformity of the aqueous menstruum in the reactor. The deep, MLD tank reactor may contain baffles or other static flow directing devices. Preferred processes for anaerobic fermentation of syngas to produce oxygenated organic compound are disclosed in U.S. patent application Ser. No. 13/243,426, filed Sep. 23, 2011, hereby incorporated by reference in its entirety.

If a jet loop reactor is used as the deep, tank reactor, one or more vertical tubes may be used in the deep tank reactor. It is not essential that these tubes extend the entire height of the aqueous menstruum. Positioning of treated gas injectors can be used to direct the flow around the loop. Preferably, the gas injectors are positioned at the top of a tube to direct the aqueous menstruum and microbubble dispersion downwardly. Thus, the initial static head, and the driving force for mass transfer of carbon monoxide into the liquid phase, is lower than that if the gas feed were introduced at a bottom portion of the deep, tank reactor.

Preferred start-up procedures for deep, tank reactors using injectors to supply the gas feed are disclosed in U.S. patent application Ser. No. 13/243,159, filed Sep. 23, 2011, hereby incorporated by reference in its entirety. The processes involve increasing both the volume of the aqueous menstruum and the density of the microorganism culture in the aqueous menstruum during start up while modulating the supply of gas feed to achieve both robust growth of the microorganism culture while avoiding the risk of carbon monoxide inhibition.

Especially for commercial scale operations, it may be desired to pre-react the gas feed to a deep, tank reactor to reduce the risk of carbon monoxide inhibition. The pre-reactor may be of any suitable configuration including, but not limited to, bubble column reactors, especially bubble column reactors having an aqueous menstruum height of less than about 10 meters, preferably less than about 5 meters; jet loop reactors; stirred tank reactors; trickle bed reactors; biofilm reactors; and static mixer reactors including, but not limited to, pipe reactors. The pre-reaction often converts between about 10 and 40 percent of the carbon monoxide in the gas feed to oxygenated organic compound. A pre-reaction operation is disclosed in U.S. patent application Ser. No. 13/243,347, filed Sep. 23, 2011, hereby incorporated by reference in its entirety.

Product Recovery:

The fermentation vessel may have added from time to time or continuously one or more streams of water, nutrients or adjuvants, and microorganisms. A portion of the aqueous menstruum is withdrawn from time to time or continuously from the reactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. US 2009/0215139 A1 shows an arrangement for a product recovery reactor that recovers an ethanol product from a bioreactor, herein incorporated by reference in its entirely.

Carbon Dioxide Removal:

Carbon dioxide may be removed from at least one of the aqueous menstruum in a reactor or from the off-gas from a reactor where the off-gas is recycled or passed to a subsequent fermentation reactor. Any suitable carbon dioxide removal process may be used including amine extraction, alkaline salt extractions, water absorption, membrane separation, adsorptions/desorption, and physical absorption in organic solvents. Considerable flexibility exists in the carbon dioxide removal step in that certain amounts of carbon dioxide are to be fed to the sequential reactor. In preferred aspects of the invention, the off-gas after carbon dioxide removal will contain at least about 15, say, between 15 and 50, mole percent of total hydrogen and carbon monoxide. Preferably the carbon dioxide concentration in the off-gas after carbon dioxide removal is between about 2 and 40, more preferably between about 5 or 10 and 20, mole percent. The off-gas after carbon dioxide removal may contain at least about 5, and often about 10 to 20, mole percent nitrogen.

A preferred process for removal of carbon dioxide from gases is by contacting the gas with an aqueous solution containing oxygenated organic compound. This process for removing carbon dioxide from gas to be fed to a reactor, including between sequential fermentation stages, is disclosed in U.S. Patent application No. 2008/0305539, filed Jul. 23, 2007, herein incorporated by reference in its entirety. See also, U.S. patent application Ser. No. 12/826,991, filed Jun. 30, 2010, herein incorporated by reference in its entirety, which discloses contacting a gas stream with a mixture of water and a surface active agent under pressure to sorb carbon dioxide and phase separating the gas and liquid stream to provide a gas stream with reduced carbon dioxide concentration to be used a feed to a reactor. United States published patent application 2008/0305539 A1 discloses the use of membranes to remove carbon dioxide from a membrane supported fermentation system to prevent dilution of concentrations of carbon monoxide and hydrogen in a multistage system.

If desired, a portion of the carbon dioxide dissolved in the liquid phase of the aqueous menstruum can be removed. Any convenient unit operation for carbon dioxide removal can be used, but the preferred operation is separation by reducing the pressure to atmospheric or lower pressure to flash carbon dioxide gas from the liquid phase.

DRAWINGS

Figure 1:
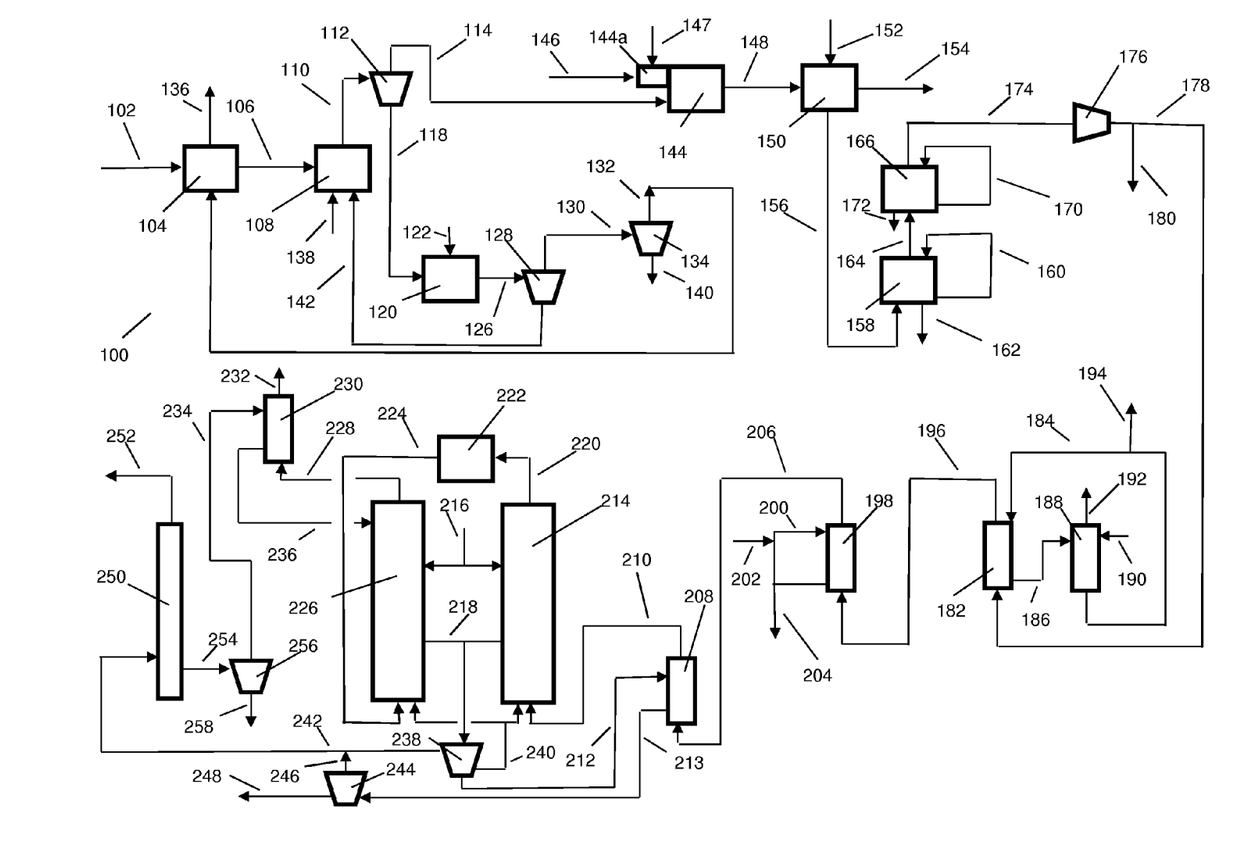
FIG. 1 is a schematic representation of apparatus suitable to carry out the processes of this invention.

A general understanding of the invention and its application may be facilitated by reference to FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other oxygenated products such as acetic acid, butanol, propanol and acetone.

The discussion of the drawings also encompasses a description of a computer simulation of a process producing 4530 kilograms of ethanol per hour.

Conveyor line 102 provides biomass to the process for conversion to ethanol. For purposes of the discussion, the biomass is wood chips. About 20,600 kilograms per hour of wood chips having a moisture content of about 40 to 50 mass percent are supplied via line 102 to dryer 104. Dryer 104 uses direct heat exchange with hot gases from line 132 to dry the wood chips. The dried wood chips now containing about 15 to 20 mass percent water are conveyed via line 106 to the gasification unit. The gases used for the drying are exhausted from dryer 104 via line 136.

The gasification unit may be of any suitable design. For purposes of illustration herein, a gasification unit is an indirect gasification unit having (i) gasification reactor 108 in which the biomass is contacted with a recirculating, heat transfer medium (for illustration, sand) and steam, and (ii) combustion reactor 120 in which char produced in the gasification reactor is combusted and sand reheated for recycle to gasification reactor 108. In further detail, the dried wood chips are passed via line 106 to gasification reactor 108. Gasification reactor 108 contains hot sand to provide the heat for the gasification, and the sand may also provide some catalytic activity. Also steam is provided to gasification reactor 108 via line 138 for reaction with the biomass. Crude syngas exits gasification reactor 108 at a temperature between about 830° C. and 870° C. and a pressure of about 135 KPa absolute. Char and sand are also withdrawn with the crude syngas. Tars may exist on the char and the sand. Line 110 directs the effluent from gasification reactor 108 to cyclone 112.

Cyclone 112 serves to separate the solids from the crude syngas. The crude syngas passes from cyclone 112 to partial oxidation reactor 144 via line 114. The solids separated in cyclone 112 are passed via line 118 to combustion reactor 120. Air is provided via line 122 to combustion reactor 120. The air may be preheated to facilitate the combustion. Char is combusted in combustion reactor 120 to reheat the sand to a temperature of between about 1020° C. and 1100° C. The combustion gases and reheated sand are passed to cyclone 128 via line 126. The reheated sand that is separated by cyclone 128 is passed to gasification reactor 116 via line 142. The hot combustion gases and ash from cyclone 128 are exhausted via line 130 and passed to cyclone 134. Ash is removed from cyclone 134 via line 140. The hot combustion gases are exhausted from cyclone 134 through line 132 and may be used for preheating the combustion air fed to combustion reactor 120 and then for drying the biomass.

The hot, crude syngas in line 114 contains about 42 mole percent hydrogen, 25 mole percent carbon monoxide and 19 mole percent carbon dioxide. (All gas compositions set forth herein are on an anhydrous basis unless otherwise specified.) Hot heat transfer particles are withdrawn from gas conditioning reactor 116 via line 132 and passed to gasification reactor 108 to provide heat for the gasification.

The hot, crude syngas in line 114 is passed to partial oxidation reactor 144. Partial oxidation reactor 144 may be of any suitable design. As shown in FIG. 1, partial oxidation reactor 144 is also fed a mixture of natural gas supplied by line 146 and oxygen supplied by line 147. The mixture is formed in section 144a of partial oxidation reactor 144 under conditions such that essentially all of the natural gas is oxidized prior to the mixture combining with the hot, crude syngas. About 260 kilograms per hour of natural gas are supplied and about 2000 kilograms of oxygen are supplied. The temperature of the partial oxidation is between about 1400° C. and 1450° C. Partially-oxidized syngas exits partial oxidation reactor 144 via line 148. The partially-oxidized syngas contains about 46 mole percent hydrogen, 41 mole percent carbon monoxide, 12 mole percent carbon dioxide and 0.15 mole percent methane.

The partially oxidized syngas is directed by line 148 to waste heat recovery boiler 150. Water is provided to waste heat recovery boiler 150 by line 152 and steam at a pressure of about 1030 KPa gauge is produced and withdrawn via line 154. This steam can be used as the steam source for gasification reactor 108 and for reboiler heat for ethanol distillation and for other uses within the process. The partially-oxidized syngas is cooled to about 135° C. in waste heat recovery boiler 150 and is passed via line 156 to first stage scrubber 158. The partially-oxidized syngas is at a pressure of about 35 KPa gauge.

The first stage scrubber is in essence a quench tower with water being sprayed to contact an up-flow of syngas. It should be understood that the contact time between the liquid and gas phases need only be relatively short in order to effect the sought cooling. If desired, longer contact times can be used to increase removal of water soluble components such as hydrogen sulfide, hydrogen cyanide, and the like from the syngas.

First stage scrubber 158 is depicted as a quench tower in which water recirculated in line 160 from the bottom of first stage scrubber 158 is sprayed at the top to contact and cool the partially-oxidized syngas. Line 160 contains a heat exchanger to cool the recirculating water. Condensate from the bottom of first stage scrubber 158 is withdrawn via line 162 and can be sent to waste water treatment. The partially-oxidized syngas is then passed via line 164 to second stage scrubber 166 in which water recirculated in line 170 from the bottom of second stage scrubber is sprayed at the top to contact and cool the partially-oxidized syngas. Condensate is withdrawn via line 172 from second stage scrubber 166.

The partially-oxidized syngas is cooled to about 35° C. and exits second stage scrubber via line 174 and is passed to compressor 176. The function of compressor 176 will depend upon whether the syngas is directly fed to fermentor 214 or must provide the syngas at a pressure suitable for additional cleanup operations. As shown, the syngas is directed to a water pressure swing absorption operation. Accordingly, the pressure of the syngas is increased to about 750 KPa gauge and the compressed syngas exits via line 178. Due to the increase in pressure condensate is formed and is removed from the compressed syngas through line 180.

FIG. 1 depicts the use of both a water pressure swing absorption and a permanganate oxidizer. This is for purposes of illustration. In practice neither or only one of these optional cleanup operations for the syngas would typically be used unless very high purity syngas is sought for the fermentation. Line 178 directs the syngas to absorption column 182 of the water pressure swing adsorption unit. Water at a temperature of about 7° C. is provided to the absorption column via line 184. The water, if desired, can contain other components to assist in the removal of components from the syngas such as buffers and reactants such as aldehydes, hypochlorites, peroxygenates, and the like. The spent water absorbent exits absorption column via line 186 and is passed to desorption column 188. Desorption column is operated at about atmospheric pressure and a temperature of about 7° C. Desorbed gases exit desorption column 188 via line 192. The rejuvenated water sorbent is withdrawn from desorption column via line 184 for return to absorption column 182. Make-up water is provided to desorption column 188 by line 190. A purge stream is removed from line 184 through line 194. Syngas exits absorption column 182 via line 196 and is directed to permanganate oxidizer 198.

Permanganate oxidizer contains a column of water having about 500 ppm (mass) of sodium permanganate dissolved therein and operates at a temperature of about 38° C. and pressure of about 750 KPa gauge. The water solution is recirculated via line 200. Manganese dioxide, a co-product of the oxidation, is filtered from the recirculating water solution and removed via line 204. Make-up sodium permanganate is added via line 202.

The treated syngas is withdrawn from permanganate oxidizer 198 via line 206 and directed to sacrificial reactor 208. Sacrificial reactor 208 is optional and frequently serves to mitigate the risk of any toxins to the microorganisms passing into the fermentation reactor due to an upset during the production and cleanup of the syngas. Sacrificial reactor 208 contains aqueous fermentation medium containing microorganisms being purged from the fermentation operation. Purging of microorganisms is used to retain an advantageous average cell retention time in the fermentation reactors. Sacrificial reactor is maintained under fermentation conditions, e.g., a temperature of about 38° C. and will result in the bioconversion of syngas to ethanol subject to the microorganisms not being rendered inactive or killed by a toxin. Aqueous fermentation medium is provided to sacrificial reactor 208 via line 212 and aqueous fermentation menstruum is withdrawn via line 213. Ethanol is recovered from the withdrawn fermentation medium as will be discussed later.

Syngas is withdrawn from sacrificial reactor 208 via line 210 and is used as the gas feed for anaerobic fermentation to make ethanol. The fresh feed, for purposes of illustration, contains about 51 mole percent hydrogen, 45 mole percent carbon monoxide, 3 mole percent carbon dioxide, about 0.2 mole percent methane, about 5 ppm (mole) acetylene, about 15 ppm (mole) ethylene, about 10 ppm (mole) nitric oxide, and less than 1 ppm (mole) hydrogen cyanide (all on an anhydrous basis).

Any suitable anaerobic fermentation process can be employed. For purposes of illustration, a fermentation process using sequential deep, bubble column reactors is discussed. It is also possible to use a single stage fermentation reactor system. As shown, the fresh gas feed is passed via line 210 to bubble column 214. Bubble column 214 contains aqueous fermentation menstruum at a depth of about 20 meters and is maintained at a temperature of about 38° C. The gas feed is injected at the bottom of bubble column 214 using slot injectors and aqueous menstruum as the motive fluid. The injectors provide microbubbles. Nutrients and make-up water are provided to bubble column 214 via line 216. Aqueous menstruum is removed from bubble column 214 via line 218 for product recovery and passed to centrifuge 238. The rate of aqueous menstruum removal is sufficient to maintain an ethanol concentration in bubble column 214 at about 2.5 mass percent. About 60 percent of the hydrogen in the gas feed and 90 percent of the carbon monoxide in the gas feed are consumed in bubble reactor 214. Centrifuge 238 provides a supernatant liquor containing ethanol which is directed to the distillation operation as will be discussed later. A concentrated microorganism-containing stream is produced by centrifuge 238 and a portion is returned to bubble column 214 via line 240 and another portion containing the cells intended to be purged, is passed to line 212 for transport to sacrificial reactor 208. While only a single bubble column 214 and centrifuge 238 is depicted, it is understood that in practice multiple bubble columns 214 and centrifuges 238 will be used. Moreover, the centrifuges are typically dedicated to a single reactor to prevent cross contamination.

Off-gas is withdrawn from the top of bubble column 214 via line 220. The off-gas contains about 36 mole percent hydrogen, 8 mole percent carbon monoxide, 54 mole percent carbon dioxide, 0.5 mole percent methane, and 1 mole percent nitrogen. The off-gas is passed to carbon dioxide removal unit 222 which is a water pressure swing absorption operation and reduces the carbon dioxide concentration to about 15 to 20 mole percent and is passed to secondary bubble column 226. Secondary bubble column 226 contains aqueous fermentation menstruum at a depth of about 20 meters and is maintained at a temperature of about 38° C. The gas feed is injected at the bottom of secondary bubble column 226 using slot injectors and aqueous menstruum as the motive fluid. The injectors provide microbubbles. Nutrients and make-up water are provided to bubble column 226 via line 216. Aqueous menstruum is removed from bubble column 226 via line 218 for product recovery and passed to centrifuge 238. The rate of aqueous menstruum removal is sufficient to maintain an ethanol concentration in bubble column 214 at about 2.5 to 3.0 mass percent. Centrifuge 238 provides a supernatant liquor containing ethanol which is directed to the distillation operation as will be discussed later. A concentrated microorganism-containing stream is produced by centrifuge 238 and a portion is returned to bubble column 226 via line 240 and another portion containing the cells intended to be purged, is passed to line 212 for transport to sacrificial reactor 208. While only a single centrifuge 238 is depicted, it is understood that in practice multiple centrifuges 238 will be used. Moreover, the centrifuges are typically dedicated to a single reactor to prevent cross contamination.

The off-gas from secondary bubble column 226 is passed by line 228 to tail gas scrubber 230 for removal of ethanol. Tail gas scrubber 230 uses the supernatant distillation bottoms from the distillation operation provided by line 234 to remove the ethanol. The treated gas exits tail gas scrubber via line 232 and can be passed to a thermal oxidation unit to provide heat for drying the wood chips. The spent distillation bottoms in tail gas scrubber 230 is withdrawn via line 236 and returned to secondary bubble column 226.

Returning to sacrificial reactor 208, the withdrawn aqueous fermentation medium is passed via line 213 to centrifuge 244. The supernatant liquid is passed from centrifuge 244 via line 246 to line 242 which transports the supernatant liquor from centrifuge 238 to the distillation operation. The solids are removed from centrifuge 244 via line 248 and passed to waste treatment.

Line 242 carries the combined supernatant liquors to distillation column 250 for ethanol recovery. Ethanol (about 92 to 94 weight percent) is recovered at the top of column 250 and is directed via line 252 to product storage or additional operation such as molecular sieve treatment and denaturing for a salable product. About 900 kilograms of distillate are produced per hour.

Distillate bottoms are removed from distillation column 250 by line 254 which directs them to hydrocyclone 256. The supernatant liquid from hydrocyclone 256 is passed via line 234 to tail gas scrubber 230. The solids are removed from hydrocyclone 256 via line 258.

It is claimed:

1. A partially-oxidized syngas for production of oxygenates by anaerobic microorganisms having a Component Composition comprising:
   (a) hydrogen and carbon monoxide wherein the mole ratio of hydrogen to carbon monoxide is between about 0.4:1 to 1.5:1 and wherein hydrogen and carbon monoxide comprise at least about 70 mole percent of the syngas composition;
   (b) between about 0.1 and 1.0 mole percent methane;
   (c) between about 1 and 50 ppm (mole) acetylene;
   (d) between about 10 and 100 ppm (mole) ethylene;
   (e) between about 0.1 and 50 ppm (mole) hydrogen cyanide;
   (f) between about 3 and 30 mole percent carbon dioxide; and
   (g) between about 2 and 100 ppm (mole) benzene.

2. The syngas composition of claim 1 in which the mole ratio of hydrogen to carbon monoxide is between about 0.8:1 and 1.3:1.

3. The syngas composition of claim 1 in which hydrogen and carbon monoxide comprise at least about 80 mole percent of the syngas composition on a Component Composition basis.

4. The syngas composition of claim 1 containing between about 10 and 70 ppm (mole) ethylene on a Component Composition basis.

5. The syngas composition of claim 1 in which carbon dioxide comprises on a Component Composition basis between about 5 and 20 mole %.

6. The syngas composition of claim 1 containing between about 20 ppm (mole) and 300 ppm (mole) hydrogen sulfide on a Component Composition basis.

7. The syngas composition of claim 1 containing on a Component Composition basis between 25 to 65 mole % carbon monoxide.

8. The syngas composition of claim 1 containing on a Component Composition basis between 35 to 60 mole % hydrogen and at least 80 mole % hydrogen and carbon monoxide; and wherein the mole ratio of hydrogen to carbon monoxide is between about 0.8:1 and 1.3:1; of the syngas composition on a Component Composition basis.

9. The syngas composition of claim 1 containing on a Component Composition basis between 0.5 ppm (mole) to 1000 ppm (mole) nitric oxide.

10. The syngas composition of claim 1 containing on a Component Composition basis between 0.1 and 15 mole % nitrogen.

11. The syngas composition of claim 1 containing on a Component Composition basis between 1 to 500 ppm (mole) of at least one of tars or naphthalene.

12. The syngas composition of claim 1 containing on a Component Composition basis between 0.1 to 25 ppm (mole) carbonyl sulfide.

13. The syngas composition of claim 1 containing on a Component Composition basis between 10 to 7,500 ppm (mole) ammonia.

14. The syngas composition of claim 1 containing on a Component Composition basis between 10 to 10,000 ppm (mole) ammonia.

15. The syngas composition of claim 1 containing on a Component Composition basis between 2 to 30 ppm (mole) hydrogen cyanide.

16. The syngas composition of claim 6 containing on a Component Composition basis between 10 and 70 (ppm mole) ethylene, between 25 to 65 mole % hydrogen, and between 0.5 to 20 ppm (mole) carbonyl sulfide.

17. A partially-oxidized syngas for production of oxygenates by anaerobic microorganisms having a Component Composition comprising:
   (a) hydrogen and carbon monoxide wherein the mole ratio of hydrogen to carbon monoxide is between about 0.4:1 to 1.5:1 and wherein hydrogen and carbon monoxide comprise at least about 70 mole percent of the syngas composition;
   (b) between about 0.1 and 1.0 mole percent methane;
   (c) between about 1 and 50 ppm (mole) acetylene;
   (d) between about 10 and 70 ppm (mole) ethylene;
   (e) between about 0.1 and 50 ppm (mole) hydrogen cyanide;
   (f) between about 3 and 30 mole percent carbon dioxide;
   (g) between about 20 ppm (mole) and 300 ppm (mole) hydrogen sulfide;
   (h) between about 2 and 100 ppm (mole) benzene;
   (i) between 25 to 65 mole % hydrogen; and
   (j) between 0.5 to 20 ppm (mole) carbonyl sulfide;
   wherein the syngas does not adversely affect microbial fermentation with the anaerobic microorganisms.

18. A partially-oxidized syngas for production of oxygenates by anaerobic microorganisms having a Component Composition comprising:
   (a) hydrogen and carbon monoxide wherein the mole ratio of hydrogen to carbon monoxide is between about 0.4:1 to 1.5:1 and wherein hydrogen and carbon monoxide comprise at least about 70 mole percent of the syngas composition;
   (b) between about 0.1 and 1.0 mole percent methane;
   (c) between about 1 and 50 ppm (mole) acetylene
   (d) between about 10 and 100 ppm (mole) ethylene;
   (e) between about 0.1 and 30 ppm (mole) hydrogen cyanide;
   (f) between about 3 and 30 mole percent carbon dioxide;
   (g) between about 25 and 65 mole percent carbon monoxide;
   (h) between about 25 and 65 mole percent hydrogen;
   (i) between about 2 and 100 ppm (mole) benzene;
   (j) between about 20 and 300 ppm (mole) hydrogen sulfide; and,
   (k) between about 0.1 and 30 ppm (mole) hydrogen cyanide.

19. A partially-oxidized and cleaned syngas for production of oxygenates by anaerobic microorganisms having a Component Composition comprising:
   (a) hydrogen and carbon monoxide wherein the mole ratio of hydrogen to carbon monoxide is between about 0.4:1 to 1.5:1 and wherein hydrogen and carbon monoxide comprise at least about 70 mole percent of the syngas composition;
(b) between 0.1 and 1.0 mole percent methane;
(c) between about 0.1 and 100 ppm (mole) acetylene
(d) between about 0.1 and 50 ppm (mole) ethylene;
(e) between about 0.001 and 2 ppm (mole) hydrogen cyanide; and
(f) between 3 and 15 mole percent carbon dioxide.

* * * * *